(12) United States Patent
Roeber

(10) Patent No.: US 8,742,237 B1
(45) Date of Patent: Jun. 3, 2014

(54) HAPLOID-INDUCER CORN LINE DESIGNATED AX6012

(75) Inventor: Frank K. Roeber, Baden-Baden (DE)

(73) Assignee: Agrigenetics, Inc., Indianapolis, IN (US)

( * ) Notice: Subject to any disclaimer, the term of this patent is extended or adjusted under 35 U.S.C. 154(b) by 0 days.

(21) Appl. No.: 13/442,173

(22) Filed: Apr. 9, 2012

Related U.S. Application Data

(60) Provisional application No. 61/472,656, filed on Apr. 7, 2011.

(51) Int. Cl.
*A01H 5/00* (2006.01)
*A01H 5/10* (2006.01)
*A01H 1/02* (2006.01)

(52) U.S. Cl.
USPC ...................................... 800/320.1; 800/275

(58) Field of Classification Search
None
See application file for complete search history.

(56) References Cited

U.S. PATENT DOCUMENTS

| 5,523,520 A | 6/1996 | Hunsperger et al. |
| 6,025,547 A | 2/2000 | Stucker |
| 6,096,953 A | 8/2000 | Hoffbeck |
| 7,714,213 B2 * | 5/2010 | Stelpflug et al. ........... 800/320.1 |

OTHER PUBLICATIONS

Allard, In Principles of Plant Breeding. John Wiley & Sons, Inc. pp. 155-156, 1960.
Phillips, et al., In Corn and Corn Improvement, ASA Monograph No. 18, 3rd edition, pp. 345, 358, 1988.
Eshed, et al., Genetics (1996), vol. 143, pp. 1807-1817.
Kraft, et al., Theoretical Applied Genetics (2000), vol. 101, pp. 323-326.
Murray, et al., Proceedings of the 43rd Annual Corn and Sorghum Industry Research Conferenc, vol. 43, p. 72-87, 1988.

* cited by examiner

*Primary Examiner* — Shubo (Joe) Zhou
*Assistant Examiner* — Keith Robinson
(74) *Attorney, Agent, or Firm* — Eric J. Kraus

(57) ABSTRACT

A haploid-inducer corn line, designated AX6012, the plants and seeds of the haploid-inducer corn line AX6012, methods for producing a corn plant, either inbred or hybrid, produced through use of the haploid-inducer corn line AX6012 are disclosed. This invention also relates to methods for generating homozygous diploid corn plants from heterozygous diploid corn plants.

16 Claims, No Drawings

HAPLOID-INDUCER CORN LINE DESIGNATED AX6012

CROSS-REFERENCE TO RELATED APPLICATIONS

This application claims the benefit of U.S. Provisional Application No. 61/472,656, filed on Apr. 7, 2011 which is expressly incorporated by reference herein.

FIELD OF THE INVENTION

The present invention generally relates to plant breeding and generating haploid corn plants. In particular, the invention relates to a haploid-inducer corn line designated AX6012 that includes plants and seeds of haploid-inducer corn line AX6012. Methods for generating homozygous diploid corn plants from heterozygous diploid corn plants are an integral part of this invention as are the resultant corn plants including the plant parts and seeds and hybrid corn plants produced therefrom.

BACKGROUND OF THE INVENTION

Corn (*Zea mays* L.) is the most important and abundant crop produced in the United States. Corn is used as human food, livestock feed, and as raw material in industry. The food uses of corn include kernels for human consumption, dry milling products such as grits, meal and flour, and wet milling products such as corn starch, corn syrups, and dextrose. Corn oil recovered from corn germ is a by-product of both dry and wet milling industries. Both grain and non-grain portions of corn plants are used extensively as livestock feed, primarily for beef cattle, dairy cattle, hogs, and poultry.

Corn is used to produce ethanol while corn starch and flour are used in the paper and textile industries. Corn is also used in adhesives, building materials, foundry binders, laundry starches, explosives, oil-well muds, and other mining applications. Plant parts other than the grain of corn are also used in industry; for example, stalks and husks are made into paper and wallboard and cobs are used for fuel and to make charcoal.

The goal of a corn breeder is to improve a corn plant's performance and therefore, its economic value by combining various desirable traits into a single plant. Improved performance is manifested in many ways. Higher yields of corn plants contribute to a more abundant food supply, a more profitable agriculture and a lower cost of food products for the consumer. Improved quality makes corn kernels more nutritious. Improved plant health increases the yield and quality of the plant and reduces the need for application of protective chemicals. Adapting corn plants to a wider range of production areas achieves improved yield and vegetative growth. Improved plant uniformity enhances the farmer's ability to mechanically harvest corn.

Corn is a monoecious plant, i.e., corn has imperfect flowers—male, pollen-producing flowers and separate female, pollen-receiving flowers on the same plant. The male flowers are located at the top of the plant in the tassel, and the female flowers are located about midway up the stalk in the ear shoot. Each male flower has three anthers and each female flower includes a husk that envelops the cob and silks that emerge from the end of the cob and husks. Pollination is consummated by transfer of pollen from the tassels of the male flower to the silks of the female flowers.

Because corn has separate male and female flowers, corn breeding techniques take advantage of the plant's ability to be bred by both self-pollination and cross-pollination. Self-pollination occurs when pollen from the male flower is transferred to a female flower on the same plant. Cross-pollination occurs when pollen from the male flower is transferred to a female flower on a different plant.

A plant is sib-pollinated (a type of cross-pollination) when individuals within the same family or line are used for pollination (i.e. pollen from a family member plant is transferred to the silks of another family member plant). Self-pollination and sib-pollination techniques are traditional forms of inbreeding used to develop new inbred corn lines but other techniques exist to accomplish inbreeding. New inbred corn lines are developed by inbreeding heterozygous plants and practicing selection for superior plants for several generations until substantially homozygous plants are obtained. During the inbreeding process with corn, the vigor of the lines decreases and after a sufficient amount of inbreeding, additional inbreeding merely serves to increase seed of the developed inbred. Inbred corn lines are typically developed for use in the production of hybrid corn lines.

Natural, or open pollination, occurs in corn when wind blows pollen from the tassels to the silks that protrude from the tops of the ear shoot and may include both self- and cross-pollination. Vigor is restored when two different inbred lines are cross-pollinated to produce the first generation ($F_1$) progeny. A cross between two defined homozygous inbred corn plants always produces a uniform population of heterozygous hybrid corn plants and such hybrid corn plants are capable of being generated indefinitely from the corresponding inbred seed supply.

When two different, unrelated inbred corn parent plants are crossed to produce an $F_1$ hybrid, one inbred parent is designated as the male, or pollen parent, and the other inbred parent is designated as the female, or seed parent. Because corn plants are monoecious, hybrid seed production requires elimination or inactivation of pollen produced by the female parent to render the female parent plant male sterile. This serves to prevent the inbred corn plant designated as the female from self-pollinating. Different options exist for controlling male fertility in corn plants such as manual or mechanical emasculation (or detasseling), genetic male sterility, and application of gametocides. Incomplete removal or inactivation of the pollen in the female parent plant provides the potential for inbreeding which results in the unwanted production of self-pollinated or sib-pollinated seed. Typically, this seed is unintentionally harvested and packaged with hybrid seed.

The development of new inbred corn plants and hybrid corn plants is a slow, costly interrelated process that requires the expertise of breeders and many other specialists. The development of new hybrid corn varieties in a corn plant breeding program involves numerous steps, including: (1) selection of parent corn plants (germplasm) for initial breeding crosses; (2) inbreeding of the selected plants from the breeding crosses for several generations to produce a series of inbred lines, which individually breed true and are highly uniform; and, (3) crossing a selected inbred line with an unrelated line to produce the $F_1$ hybrid progeny having restored vigor.

Inbred corn plants and other sources of corn germplasm are the foundation material for all corn breeding programs. Despite the existence and availability of numerous inbred corn lines and other source germplasm, a continuing need still exists for the development of improved germplasm because existing inbred parent corn lines lose their commercial competitiveness over time.

Traditional plant breeding to include parental lines for desirable traits involves crossing selected parental lines to introduce those desirable traits into the progeny of the cross. In a crossing-based approach, often, not only the desirable trait is transferred to the progeny but some randomization of the genomes of both parental lines occurs. This results in a wide segregation and variation of morphology and other traits of the progeny, which are not predictable. The uncontrolled variation renders the progeny selection process very long, cumbersome and laborious especially if the desired traits are not expressed early in the progeny or if the desired trait is recessive.

In an effort to minimize random variation, breeders prefer homozygous parental lines (inbreds) so that the genetic makeup of the $F_1$ generation is more predictable. The inbreds with a desirable trait are generated by back-crossing a heterozygote with its parental lines, followed by segregation selection and repeated back-crossing. However, this repeated back-crossing is also very long, usually up to 6-7 times, depending on the plant, would produce a homozygous plant with the desired trait. Of course, the time scale involved here is dictated by the rate at which plants grow to maturity and set seed and several years can be necessary to produce the desired homozygous parent line.

Haploid plants contain one half of the usual complement of genes. Normal plants are diploid in that they have two complete sets of chromosomes, one from each parent. Haploid plants are capable of growing to maturity but are generally sterile. There are several known methods of generating haploid plants. One method is to generate maternal haploid plants by means of crossing a female parent with a haploid-inducer male parent, which results in a portion of the fertilized embryos being haploid for maternal chromosomes. These haploid embryos or subsequent plants can be selected using phenotypic markers. Thereafter, homozygous diploid plants are produced by the doubling of a set of chromosomes (1N) from the haploid tissue by exposure to a doubling agent, such as colchicine, nitrous oxide gas, heat treatment, and trifluralin. See, e.g., Wan et al., "Efficient Production of Doubled Haploid Plants Through Colchicine Treatment of Anther-Derived Maize Callus", Theoretical and Applied Genetics, 77:889-892, 1989 and U.S. Patent Application No. 20030005479 the disclosure of which is expressly incorporated herein by reference. The doubling of chromosomes produces completely homozygous diploid plants, called doubled haploids. This method of doubled-haploid plant breeding eliminates the need for multigeneration inbreeding to produce a segregating population of inbred lines for evaluation, saving years of time.

By producing doubled-haploid progeny, the number of possible gene combinations for inherited traits is more manageable. Thus, an efficient doubled haploid technology can significantly reduce the time and the cost of inbred and cultivar development. The present invention addresses this need by providing a novel inducer corn line designated AX6012 that contributes to the production of haploid plants that can be subsequently doubled to yield highly uniform inbred lines.

DETAILED DESCRIPTION OF THE INVENTION

I. Definitions of Plant Characteristics

In the description and examples that follow, a number of terms are used. To provide a clear and consistent understanding of the specification and claims, including the scope to be given such terms, the following definitions are provided.

Anther Color: Recorded at the time of pollen shed when anthers are actively dehiscing pollen as a standard color name and Munsell color code.

Anthocyanin in Brace Roots: This is a relative rating of the expression of anthocyanin in the brace roots (1=none, 2=faint, 3=50% purpling/moderate, and 4=dark) recorded two weeks after flowering.

Aphid Attractiveness: This represents the relative level of aphid numbers found on an emerging tassel up to and during the period of pollen shed rated as high, average or none.

Cob Color: Recorded as a standard color name and Munsell color code.

Doubled Haploid: An embryo that contains two sets of chromosomes, the first set from the maternal parent and the second set duplicated from the first by natural or chemical means.

Ears Per Stalk: The total number of ears with seed set on each plant.

Ear Height: This is the distance in centimeters from the ground to the highest placed ear node point of attachment of the ear shank of the uppermost developed ear on the stalk.

Ear Leaves: Ear leaves are defined as one or more distinct ear leaves on ear husks at flowering (usually >0.25 to 0.5") represented as present or absent. This characteristic may be difficult to determine, may be environmentally influenced, and is not recorded as present unless the ear leaves are present in sufficient size or on several plants in the middle of the row.

Ear Length: This is the length of an unhusked ear from the butt to the tip in centimeters.

Ear Position At Dry Husk: This represents the relative direction of the top ear observed 65 days after pollinating while still attached to the plant rated as 1=upright, 2=horizontal and 3=pendent.

Ear Taper: This represents the relative taper of the unshelled ear rated as slight or nearly straight (1), average (2), or extreme or conical (3).

Endosperm Type: Endosperm is the material in the region of the kernel between the germ and the seed coat and is rated on the following scale: 1=sweet, 2=extra sweet (sh2), 3=normal starch, 4=high amylase starch, 5=waxy, 6=high protein, 7=high lysine, 8=supersweet (se), 9=high oil and 10=other-specify.

50% Pollen (GDU from Planting): The number of GDUs after planting when 50% of the plants are shedding pollen.

50% Silk (GDU from Planting): The number of GDUs after emergence when 50% of the plants have extruded silk.

Glume Band: Recorded as absent or, if present, as a standard color name and Munsell color code.

Glume Color: Recorded after exposure to sunlight and just before extruding anthers as a standard color name and Munsell color code.

Haploid Inducer: A plant genetically capable of causing (inducing) the formation of haploid embryos after gametic fertilization.

Hard Endosperm Color: This is the color of the region of the endosperm between the floury endosperm and the aleurone layer in yellow dent corn recorded as a standard color name and a Munsell color code.

Husk Tightness: This represents the relative ability for husks to be removed either manually or through commercial production husking beds 65 days after flowering rated as loose (2), average (5) and 8 (tight).

Kernel Crown Color: This is the color of the portion of the kernel distal to the tip cap recorded as a standard color name and Munsell color code.

K Row Alignment: This is kernel row alignment and is scored as straight, slightly curved or spiral determined by standing the unshelled ear on its base and looking down at the tip.

Kernel Rows: The presence (distinct) or absence (indistinct) of defined kernel rows.

Lateral Tassel Branches: This represents the number of primary lateral tassel branches that originate from the central spike.

Leaf Color: Recorded as standard color name and Munsell color code.

Leaf Sheath Color: The Munsell or standard color of that part of the leaf originating from the plant node and running parallel to the culm or stem up to the point at which it turns away from the stem and turns into the leaf blade (typically separated by the Auricle).

Number of Kernel Rows: This is the average total number of kernel rows on the ear. If the rows are indistinct, then this value is an average number of kernels located around the circumference of the ear at the mid-point of its length.

Number of Leaves Above Ear: This represents the average number of leaves above the ear leaf.

Plant Height: This is the plant height in centimeters from the ground to the tip of the tassel.

Radicle Pigmentation: Munsell color code for seedling radicle three days after germination grown in a zero light environment.

Silk Color: Recorded 3 days after emergence using standard color name and Munsell color code.

Standard Color Names: These color names include light green, medium green, dark green, very dark green, green-yellow, pale yellow, yellow, yellow orange, salmon, pink-orange, pink, light red, cherry red, red, red and white, pale purple, purple, colorless, white, white capped, buff, tan, brown, bronze and variegated.

Tassel Length: This is the length of the tassel from the top leaf collar to the tassel tip measured in centimeters.

Tassel Type: This the tassel branch shape recorded as erect or spreading. The angle of the base of each tassel branch is used to indicate the direction of the branches. Erect longer or lighter tassels that droop over on the tip are classified as erect.

II. Inbred Corn Line AX6012

A. Inbred Corn Plant AX6012

In accordance with one aspect of the present invention, provided is a new yellow dent inbred corn seed and plants thereof designated AX6012. The present invention further relates to a method for producing inbred corn seeds that includes, but is not limited to, the steps of planting seed of inbred corn AX6012 in proximity to itself or to different seed from a same family or line, growing the resulting corn plants under self-pollinating or sib-pollinating conditions with adequate isolation, and harvesting resultant seed obtained from such inbred plants using techniques standard in the agricultural arts such as would be necessary to bulk-up seed such as for hybrid production. The present invention also relates to inbred seed produced by such a method.

In a cross between inducer corn line AX6012 and another corn plant, AX6012 is be designated as the male (pollen parent). The seed of inducer corn line AX6012 may be pre-treated to increase resistance of the seed and/or seedlings to stressed conditions, and further, the corn plants or surrounding soil may be treated with one or more agricultural chemicals before harvest. Such agricultural chemicals may include herbicides, insecticides, pesticides and the like. The present invention also relates to a corn plant that expresses substantially all of the physiological and morphological characteristics of inducer corn plant AX6012 and to a substantially homogeneous population of corn plants having all the physiological and morphological characteristics of inducer corn plant AX6012. Any corn plants produced from inducer corn plant AX6012 are contemplated by the present invention and are, therefore, within the scope of this invention. A description of physiological and morphological characteristics of inducer corn plant AX6012 is presented in Table 1.

TABLE 1

| AX6012 Phenotypic Descriptions | |
|---|---|
| Character | Value |
| 50% of plants shedding pollen(GDU) | 1308 |
| 50% of plants silking (GDU) | 1326 |
| Anther Color (Std chart color) | 13 (Cherry Red) |
| Anther Color (Munsell Code) | 2.5R 4/6 |
| Glume Color (Std chart color) | 17 (Purple) |
| Glume Color (Munsell Code) | 5R 3/2 |
| Leaf Sheath Color (Std Chart Color) | 17 (Purple) |
| Leaf Sheath Color (Std Chart Color) | 5R 3/2 |
| Silk Color (Std Chart Color) | 17 (Purple) |
| Silk Color (Munsell Code) | 2.5R 5/4 |
| Glume Band (Pr/Abs) | Abs |
| Attractive to Aphids (H, Av, N) | Av |
| Plant Ht (to tassel tip - cm) | 170 |
| Ear Ht (top ear node - cm) | 60 |
| Ear Leaves (Pr/Abs) | Pr |
| Anthocyanin in brace roots (rating) | 4 |
| Leaf Color (Std) | 3 + 17 (Dark Green with Purple Margins) |
| Leaf Color (Munsell Code) | 5GY 3/4 + 5RP 3/6 Margins |
| # Leaves Above Ear | 5 |
| Tassel Length (cm) | 37 |
| # Tassel Branches - Lateral | 14 |
| # Ears Per Stalk | 1 |
| Position of Ear at Dry Husk (rating) | n/a |
| Husk Tightness (rating) | 5 |
| Ear Length (cm) | 12 |
| # Kernel Rows | n/a |
| Kernel Rows (1 = distinct, 2 = indistinct) | 2 |
| Kernel Row Alignment | Not aligned |
| Ear Taper (1-slight, 2-average, 3 extreme) | 2 |
| Endosperm type (1-10 rating, see pg 3) | 3 |
| Cob Color (std) | 17 (Purple) |
| Cob Color (Munsell code) | 5RP 3/6 |
| Hard Endosperm (Std Color) | 17 (Purple) |
| Hard Endosperm (Munsell Code) | 5RP 3/6 |
| Kernel Crown Color (std) | 17 (Purple) |
| Kernel Crown Color (Munsell) | 5RP 3/6 |
| Tassel Type | 2 |
| Radicle Pigmentation | 5RP 7/4 to 5RP 3/10 |

It should be appreciated by one having ordinary skill in the art that, for the quantitative characteristics identified in Table 1, the values presented are typical values. These values may vary due to the environment and accordingly, other values that are substantially equivalent are also within the scope of the invention.

Inducer corn line AX6012 shows uniformity and stability within the limits of environmental influence for the traits described in Table 1. Inducer AX6012 has been self-pollinated and ear-rowed a sufficient number of generations with careful attention paid to uniformity of plant type to ensure the homozygosity and phenotypic stability necessary to use in large scale, commercial production. The line has been increased both by hand and sib-pollinated in isolated fields with continued observations for uniformity. No variant traits have been observed or are expected in inducer corn line AX6012.

The present invention also relates to one or more corn plant parts of inducer corn plant AX6012. Corn plant parts include plant cells, plant protoplasts, plant cell tissue cultures from which corn plants can be regenerated, intact genomic plant DNA, plant calli, plant clumps, and plant cells that are intact in plants or parts of plants, such as embryos, pollen, ovules, flowers, seeds, kernels, ears, cobs, leaves, husks, stalks, roots, root tips, brace roots, lateral tassel branches, anthers, tassels, glumes, silks, tillers, and the like.

B. Inducer Corn Seed Designated AX6012

A corn kernel is composed of four structural parts: (1) the pericarp, which is a protective outer covering (also known as bran or hull); (2) the germ (also known as an embryo); (3) the endosperm; and, (4) the tip cap, which is the point of attachment to the cob. Another aspect of the present invention is one or more parts of inducer corn seed AX6012, such as the pericarp of inducer corn seed AX6012 or the germ and/or the endosperm of inducer corn seed AX6012, which remain upon removal of the pericarp and adhering remnants of the seed coat.

Inducer corn seed designated AX6012 may be provided as a substantially homogeneous composition of inducer corn seed designated AX6012, that is, a composition that consists essentially of inducer corn seed AX6012. Such a substantially homogeneous composition of inducer corn seed AX6012 is substantially free from significant numbers of other inducer and/or hybrid seed so that the inducer seed forms from about 90% to about 100% of the total seed. Preferably, a substantially homogeneous composition of the inducer corn seed contains from about 98.5%, 99%, or 99.5% to about 100% of the inducer seed, as measured by seed grow outs. The substantially homogeneous composition of inducer corn seed of the invention may be separately grown to provide substantially homogeneous populations of inducer corn plants.

Corn yield is affected by the conditions to which seeds and seedlings (young plants grown from seeds) are exposed. Seeds and seedlings may be exposed to one of, or a combination of, for example, cold, drought, salt, heat, pollutants, and disease, all of which are conditions that potentially retard or prevent the growth of crops therefrom. For example, temperature extremes are typical in the upper Midwest region of the United States. Furthermore, diseases evolved from pathogens, and deterioration caused by fungi, are potentially harmful to seeds and seedlings. Thus, it is desirable to treat seeds as by coating or impregnating the seeds with compositions that render the seeds and seedlings grown therefrom more hardy when exposed to such adverse conditions.

Accordingly, another aspect of the present invention relates to a coated and/or impregnated seed or corn inducer line designated AX6012 and to coated and/or impregnated seed derived therefrom. Various agents have been used to treat seeds to increase resistance of the plants to stressed conditions, such as cold, drought, salt, and fungi. Such agents include, for example, sodium methylphenyl-pentadienate, trichloroacetic acid, polyoxyalkylene-organo-siloxane block copolymer, 5-aminolevulinic acid, salicylic acid, thiamethoxam, potassium chloride, and polyvinyl alcohol and are useful alone, or in combination in the present invention.

When pre-treating seeds according to the present invention such as before the seeds are planted, the seeds are contacted with the composition of interest, as by coating seeds, spraying seeds, and soaking seeds or a combination thereof, by methods well known to those skilled in the art.

C. Deposit Information

Applicants have made a deposit of at least 2,500 seeds of inbred corn plant AX6012 with the American Type Culture Collection (ATCC), Manassas, Va. 20110 USA, under ATCC Accession No. PTA-120461. The seeds deposited with the ATCC on Jul. 5, 2013 were taken from a deposit maintained by Agrigenetics, Inc. d/b/a Mycogen Seeds since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant(s) will maintain and will make this deposit available to the public pursuant to the Budapest Treaty.

III. Processes of Preparing Novel Corn Plants

A. Novel Homozygous Diploid Inbred Corn Plants Obtained From Inducer Corn Line AX6012

Various breeding schemes may be used to produce new inbred corn lines from inducer corn line AX6012. In one method for generating homozygous diploid corn plants from heterozygous diploid corn plants, seed of a heterozygous diploid corn plant is planted in pollinating proximity to seed of a haploid-inducer corn plant designated AX6012.

Thereafter, pollination is controlled in a manner such that the haploid-inducer corn plant designated AXC06012 pollinates the heterozygous diploid plant. For example, bags, usually plastic or glassine, applied to cover the ear shoot before the extrusion of silks provide effective control of unwanted pollination.

In a subsequent step, resultant seeds from the heterozygous diploid corn plant are harvested.

In some embodiments of the present invention, the harvested resultant seed can be preliminarily sorted based on embryo coloration into a first subset having a dark pigmented embryo and a second subset having a normal colored embryo. A dark pigmented embryo would be an indicator of a successfully generated haploid seed.

Thereafter, corn plants from the harvested resultant seeds are germinated. In embodiments of the present invention, the germination is performed on a moist substrate and is also performed in the dark.

In the next step, the generated corn plants are sorted based on root coloration into a first subset having normal root coloration and a second subset having abnormal coloration. In preferred embodiments, the abnormal root coloration is from 5RP 7/4 to 5RP 3/10 (Munsell code).

Thereafter, diploid plants are generated from the haploid plants. The diploid plants may be generated by subjecting the haploid plants to a treatment that induces chromosome doubling. Such treatments are well-known to those in the corn breeding art and include a colchicine treatment.

In another aspect of this invention a new inbred corn plant is developed by a method that includes the steps of crossing AX6012 or a hybrid made with AX6012 with another inbred corn plant having a propensity to generate haploids to produce haploid progeny plants, and selecting desirable inbred corn plants from the haploid progeny plants.

Once doubled-haploid inbred lines are created, the next step is to determine if the inbreds have any value for breeding and/or as parents in hybrid production. This is accomplished by techniques of measuring the combining ability of the new inbred plant, as well as the performance of the line itself. Combining ability refers to a line's contribution as a parent when crossed with other lines to form hybrids. Specific combining ability (SCA) refers to the ability of a line to cross to another specific inbred to form a hybrid. General combining ability (GCA) refers to the ability of a line to cross to a wide range of lines to form hybrids. The methodology of forming hybrids to evaluate an inbred line's contribution as a parent for the purpose of selecting superior lines is interchangeably known as experimental, top or test crossing.

IV. Novel Hybrid Plants

A. Novel Hybrid Seeds and Plants

In yet another aspect of the invention, processes are provided for producing corn seeds or plants, which processes generally comprise crossing a first parent corn plant with a second parent corn plant wherein at least one of the first parent corn plant or the second parent corn plant is inbred parent corn plant AX6012. In the present invention, the first inbred corn plant is AX6012 and is a male. These processes may be further exemplified as processes for preparing hybrid corn seed or plants, wherein a first inbred corn plant is crossed with a second corn plant of a different, distinct variety to provide a hybrid that has, as one of its parents, the inbred corn plant variety AX6012. In this case, a second inbred variety is selected which confers desirable characteristics when in hybrid combination with the first inbred line. In these processes, crossing will result in the production of seed. The seed production occurs regardless whether the seed is collected.

Any time the inbred corn plant AX6012 is crossed with another, different corn inbred, a first generation ($F_1$) corn hybrid plant is produced. As such, an $F_1$ hybrid corn plant may be produced by crossing AX6012 with any second inbred corn plant. Therefore, any $F_1$ hybrid corn plant or corn seed which is produced with AX6012 as a parent is part of the present invention.

In embodiments of the present invention, the first step of "crossing" the first and the second parent corn plants comprises planting, preferably in pollinating proximity, seeds of a first inbred corn plant and a second, distinct inbred corn plant. As discussed herein, the seeds of the first inbred corn plant and/or the second inbred corn plant can be treated with compositions that render the seeds and seedlings grown therefrom more hardy when exposed to adverse conditions.

A further step comprises cultivating or growing the seeds of the first and second parent corn plants into plants that bear flowers. If the parental plants differ in timing of sexual maturity, techniques may be employed to obtain an appropriate nick, i.e., to ensure the availability of pollen from the parent corn plant designated the male during the time at which silks on the parent corn plant designated the female are receptive to the pollen. Methods that may be employed to obtain the desired nick include delaying the flowering of the faster maturing plant, such as, but not limited to delaying the planting of the faster maturing seed, cutting or burning the top leaves of the faster maturing plant (without killing the plant) or speeding up the flowering of the slower maturing plant, such as by covering the slower maturing plant with film designed to speed germination and growth or by cutting the tip of a young ear shoot to expose silk.

In a preferred embodiment, the corn plants are treated with one or more agricultural chemicals as considered appropriate by the grower.

A subsequent step comprises preventing self-pollination or sib-pollination of the plants, i.e., preventing the silks of a plant from being fertilized by any plant of the same variety, including the same plant. This is preferably done in large scale production by controlling the male fertility, e.g., treating the flowers so as to prevent pollen production or alternatively, using as the female parent a male sterile plant of the first or second parent corn plant (i.e., treating or manipulating the flowers so as to prevent pollen production, to produce an emasculated parent corn plant or using as a female, a cytoplasmic male sterile version of the corn plant). This control may also be accomplished in large scale production by physical removal of the tassel from the female plant, either by pulling the tassel by hand, cutting with a rotary cutter, or pulling with a mechanical tassel pulling machine. In small scale production, bags, usually plastic or glassine, applied to cover the ear shoot prior to the extrusion of silks provide effective control of unwanted self-pollination or sib-pollination.

Yet another step comprises allowing cross-pollination to occur between the first and second parent corn plants. When the plants are not in pollinating proximity, this is done by placing a bag, usually paper, over the tassels of the first plant and another shoot bag over the ear shoot, prior to the extrusion of silk, of the incipient ear on the second plant. The bags are left in place usually overnight. Since pollen stops shedding each day and loses viability and new pollen is shed each morning, this assures that the silks are not pollinated from other pollen sources, that any stray pollen on the tassels of the first plant is dead, and that the only pollen transferred comes from the first plant. The pollen bag over the tassel of the first plant is then shaken vigorously to enhance release of pollen from the tassels and removed from the first plant. Finally, in one continuous motion, the shoot bag is removed from the silks of the incipient ear on the second plant, and the pollen bag containing the captured pollen is placed over the silks of the incipient ear of the second plant, shaken again to disperse the captured pollen, and left in place covering the developing ear to prevent contamination from any unwanted fresh airborne pollen. In large scale production, crossing is accomplished by isolated open-pollinated crossing fields whereby corn plants of the parent designated as the female, which are controlled for male fertility, are allowed to be pollinated by other plants of a different corn type where such plants are adjacent to the plants designated as the female parent.

A further step comprises harvesting the seeds, near or at maturity, from the ear of the plant that received the pollen. In a particular embodiment, seed is harvested from the female parent plant, and when desired, the harvested seed can be grown to produce a first generation ($F_1$) hybrid corn plant.

Yet another step comprises drying and conditioning the seeds, including the treating, sizing (or grading) of seeds, and packaging for sale to growers for the production of grain or forage. As with inbred seed, it may be desirable to treat hybrid seeds with compositions that render the seeds and seedlings grown therefrom more hardy when exposed to adverse conditions. Mention should be made that resulting hybrid seed is sold to growers for the production of grain and forage and not for breeding or seed production.

Still further, the present invention provides a hybrid corn plant produced by growing the harvested seeds produced on the male-sterile plant as well as grain produced by the hybrid corn plant.

A single cross hybrid is produced when two different inbred parent corn plants are crossed to produce first generation $F_1$ hybrid progeny. Generally, each inbred parent corn plant has a genotype which complements the genotype of the other inbred parent. Typically, the $F_1$ progeny are more vigorous then the respective inbred parent corn plants. This hybrid vigor, or heterosis, is manifested in many polygenic traits, including markedly improved yields and improved stalks, roots, uniformity and insect and disease resistance. It is for this reason that single cross $F_1$ hybrids are generally the most sought after hybrid. A three-way, or modified single-cross hybrid is produced from three inbred lines (or synthetics) where two of the inbred lines are crossed (A×B) and then the resulting $F_1$ hybrid is crossed with the third inbred (A×B)× C, as where a modified female is used in the cross. A modified female provides an advantage of improved seed parent yield whereas a modified male improves pollen flow. A double cross hybrid is produced from four inbred lines crossed in pairs (A×B and C×D), thereby resulting in two $F_1$ hybrids that are crossed again. Double cross hybrids are more common in countries wherein less demand exists for higher yielding single cross hybrids. Synthetic populations or crosses are developed by crossing two or more inbred lines (or hybrids, or germplasm sources) together and then employing one of many possible techniques to random mate the progeny. Random mating the progeny is any process used by plant breeders to make a series of crosses that will create a new germplasm pool from which new breeding lines can be derived. Much of the hybrid vigor exhibited by $F_1$ hybrids is lost in the next generation ($F_2$). Consequently, seed from hybrids are not typically used for planting stock.

The present invention provides $F_1$ hybrid corn plants obtained from the corn plant AX6012. The physical characteristics of exemplary hybrids produced using AX6012 as one inbred parent are set forth in Table 2-4.

EXAMPLES

The following examples are included to demonstrate certain preferred embodiments of the invention. These examples should not be construed as limitations to the claims. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention.

Example 1

Production of Haploid Maize Plants by Pollination with an Inducer Line

A haploid-inducer line, AX6012, was used as a male crossing partner (pollen donor) to pollinate a female elite maize population. Female populations containing either the Dent or Flint genetic background were used. The ears of the female parent plants were shoot-bagged before silk emergence to avoid contamination with foreign pollen. Silks of the female plants were pollinated with pollen collected from the tassel of the haploid inducer line. Ears were harvested when kernels were mature (expressing a black layer) and anthocyanin coloration was fully expressed. Ears harvested from the female plant contained kernels with haploid and diploid embryos. The haploid kernels can be distinguished from the diploid kernels, as they possess a darker pigmented embryo. Outcrosses were visually identified as containing yellow endosperm, and discarded directly on the ear after drying. One-hundred seeds were sorted and putative haploid kernels were isolated. Kernels that were identified as putative haploid kernels, containing only one set of maternal chromosomes, were present at a frequency ranging between 10-12%. These progeny were obtained and treated for production of haploid kernels.

Example 2

Selection of Putative Haploid Kernels and Chromosome Doubling of Haploid Embryos Putative Haploid Kernel (PHK) maize seeds were treated with a fungicide (4 ml Tutan, 6 ml $H_2O$ for 10 kg seeds) and germinated on a moist paper towel. Fifty seeds were lined up on a single paper towel and germinated in the dark for 3-4 days at 26-28° C. to ensure high levels of cell divisions. Germinated seedlings were selected at 3 different time points (24, 48 and 72 hours post-germination) to ensure that the chromosomal doubling treatment would occur at the right stage.

Developing roots from the seedlings were visually observed. Seedlings were inspected for pigmentation within the radicle. The seedlings which possessed pink radicles were selected and scored using the Munsell color code. Haploid seedlings which were produced using the AX6012 inducer line scored from 5RP 7/4 to 5RP 3/10 using the Munsell code.

A doubling agent was applied to the selected seedlings. Seedlings which had coleoptiles of about 2 cm were chosen. The tips of the coleoptiles were cut with a razor blade to ensure that the colchicine solution could reach the meristem tissue; cuts were made ~2 mm from the tip. The seedlings were soaked in a freshly prepared colchicine solution (0.06% colchicine and 0.5% DMSO) for 8 hours. After soaking the seedlings in the colchicine solution, the seeds were rinsed in tap water for 30 minutes.

Example 3

Screening and Identification of Doubled-Haploid Maize Plants

The seedlings were transplanted into soil within Jiffy-pots, and transferred to an adaptation greenhouse where they grew for 2.5 weeks. After this time period, the plants were adapted for field growing conditions by moving the plants outdoors for 1 week. An application of foliar fertilizer was made (Fertiactyl, Roullier Group) to support root development of the maize plants before they were transported to planting locations. After transplantation, plants were irrigated thoroughly and irrigation was repeated as needed. Before flowering, a second foliar fertilizer application (Fertilizer II, Table 2) was applied to support development of flowering organs. The maize plants were planted within a field in Germany for the 2009-2010 growing season and grown using standard agronomic practice.

Misclassified plants were identified in the field as determined by their agronomic performance (e.g., hybrid types, broader leaves, advanced vigor, size of tassel, plant height, ears with colored kernels) and red stem coloration. Misclassification rates (Table 3) were calculated accordingly; Haploid plants/Misclassified plants×100. In addition, the subsequent induction rates for the AX6012 line were calculated. The AX6012 induction rates were determined to average 10%. Induction rates of AX6012 were evaluated during its development by using a liguleless tester. Table 4 presents the induction rates of AX6012 in comparison to other known inducer lines.

TABLE 2

Components of Fertilizer II.

| Commercial Name | 500 L water/ha |
|---|---|
| Magnisal | 3 kg |
| Folicin Bor Plus | 1 L |
| Folicin Mn | 0.75 L |
| Folicin Zn | 0.75 L |
| Folicin Cu | 0.5 L |
| Phosfik | 3-5 L |
| Aminosol | 1 L |
| Folicin Mo | 15-20 gm |

TABLE 3

TABLE 3: Misclassification Rates for Inducer AX6012 (Abbreviations are as follows; Npop: Total number of plants screened; Misscl. Rate %: Percentage of misclassification; % Min: Lowest observed misclassification rate; % Max: Highest observed misclassification rate).

| Year | Inducer | Induced Germplasm | Npop | Misscl. rate % | % Min | % Max |
|---|---|---|---|---|---|---|
| 2009/10 | AX6012 | dent | 265 | 6.76 | 5.58 | 48.68 |
| | AX6012 | flint | 153 | 13.24 | 0.50 | 54.70 |
| | BRZ06 | dent | 11 | 39.31 | 3.37 | 78.28 |
| | BRZ06 | dent | 3 | 14.18 | 6.48 | 23.17 |

TABLE 4

Induction rates of AX6012 in comparison to other known maize inducer lines.

| Induction | Inducer | Induction Rate (%) | Origin/Author |
|---|---|---|---|
| Maternal | Stock6 | 2.3 (3.2*) | Coe, 1959 |
| | WS14 | 2.0-5.0 | Lashermes and Beckert, 1989 |
| | KEMS | 6.3 | Shatskaya et al., 1999 |
| | RWS | 10.0 | Röber and Geiger, 1999 |
| | UH400 | 8.0-9.0 | Schipprack, personal communication, 2002 |
| | BRZO6 | 12.3 | DowAgrosciences |
| | B-432 | 13.9* | Dankov et al., 1993 |
| | ZMS | 0.6-3.4 | Tyrnov and Zavalishina, 1984 |
| | AC'R | 5.5 | Sarkar et al., 1994 |
| | ACR | 8.3 | Sarkar, personal communication, 1995 |
| | KMS | 0.8-2.9 | Chalyk et al., 1994 |
| | PK6 | 6.0 | Bordes et al., 2003 |
| | AT-1 | 2.0-3.0 | Tyrnov, 1997 |
| | AX6012 | 10.0 | This Work |
| Paternal | W23ig | Up to 3.0 | Kermicle, 1969 |
| | W23ig | 2.6-8.0 | Kindiger and Hamann, 1993 |

+B - translocation
* = in selfs

All publications, patents and patent applications mentioned in the specification are indicative of the level of those skilled in the art to which this invention pertains. All such publications, patents and patent applications are incorporated by reference herein to the same extent as if each was specifically and individually indicated to be incorporated by reference herein.

The foregoing invention has been described in some detail by way of illustration and example for purposes of clarity and understanding. However, it should be appreciated by those having ordinary skill in the art that certain changes and modifications such as single gene modifications and mutations, somoclonal variants, variant individuals selected from large populations of the plants of the instant inbred and the like may be practiced within the scope of the invention, as limited only by the scope of the appended claims, without departing from the true concept, spirit, and scope of the invention.

What is claimed is:

1. Seed of corn haploid-inducer line designated AX6012, a sample of seed of the line having been deposited under ATCC Accession No. PTA-120461.

2. A part of the seed of claim 1 selected from the group consisting of pericarp, germ and endosperm.

3. The seed of claim 1, further comprising a coating.

4. A composition comprising the seed of claim 1.

5. A corn plant produced by growing the seed of claim 1.

6. A part of the corn plant of claim 5, selected from the group consisting of an intact plant cell, a plant protoplast, an embryo, a pollen, an ovule, a flower, a kernel, a seed, a intact genomic plant DNA, an ear, a cob, a leaf, a husk, a stalk, a root, a root tip, a brace root, a lateral tassel branch, an anther, a tassel, a glume, a tiller and a silk.

7. Pollen of the plant of claim 5.

8. An ovule of the plant of claim 5.

9. A method for generating homozygous diploid corn plants from heterozygous diploid corn plants, the method comprising the steps of:
   a.) planting a seed of a heterozygous diploid corn plant in pollinating proximity to the seed of claim 1;
   b.) controlling pollination in a manner such that the haploid-inducer corn plant designated AX6012 pollinates the heterozygous diploid plant;
   c.) harvesting resultant seeds from the heterozygous diploid corn plant;
   d.) germinating corn plants from harvested resultant seed;
   e.) sorting the generated corn plants based on root coloration into a first subset having normal root coloration and second subset having abnormal coloration; and
   f.) generating diploid plants from the haploid plants.

10. The method of claim 9, further comprising the step of sorting the harvested resultant seed based on embryo coloration into a first subset having a dark pigmented embryo and a second subset having a normal colored embryo.

11. The method of claim 9, wherein the germination was performed on a moist substrate.

12. The method of claim 11, wherein the germination was performed in the dark.

13. The method of claim 9, wherein the abnormal root coloration is from 5RP 7/4 to 5RP 3/10 (Munsell code).

14. The method of claim 9, wherein the diploid plants are generated by subjecting the haploid plants to a treatment that induces chromosome doubling.

15. The method of claim 14, wherein the treatment that induces chromosome doubling is a colchicine treatment.

16. The method of claim 9, further comprising the step of identifying and removing plants that were misclassified.

* * * * *